United States Patent [19]

Bias

[11] Patent Number: 5,000,949
[45] Date of Patent: Mar. 19, 1991

[54] HAIR GROOMING COMPOSITION

[76] Inventor: Mae D. Bias, P.O. Box 671863, Houston, Tex. 77267

[21] Appl. No.: 273,560

[22] Filed: Nov. 21, 1988

[51] Int. Cl.⁵ .......................... A61K 7/075; A61K 7/06
[52] U.S. Cl. .................................. 424/74; 424/195.1; 514/783
[58] Field of Search ........................ 424/74, 195.1, 70; 514/783

[56] References Cited

U.S. PATENT DOCUMENTS 3,227,616 1/1966 Van Wessem et al. ............. 514/783

FOREIGN PATENT DOCUMENTS 144830 2/1975 Netherlands .

Primary Examiner—Merrell C. Cashion, Jr.
Assistant Examiner—Susan S. Rucker
Attorney, Agent, or Firm—Neal J. Mosely

[57] ABSTRACT

A hair grooming composition which promotes scalp and hair health and growth comprises petroleum jelly, an oil extract of cactus, glycerin and oil of clover or other odorant. The petroleum jelly is heated in a pan with the cactus cut into small pieces and the mixture cooked until the cactus is brown and throughly extracted. The mixture is strainrd to remove cactus leaves and other solids and then mixed with glycerin and oil of clover. The product is then packaged for sale and use. The product improves scalp health and users have reported extensive regrowth of hair in bald areas.

18 Claims, No Drawings

HAIR GROOMING COMPOSITION

BACKGROUND OF THE INVENTION

1. Field of the Invention

This invention relates generally to hair grooming compositions and more particularly to grooming compositions which promote scalp and hair health and growth.

2. Brief Description of the Prior Art

The prior art includes many patents disclosing hair grooming compositions which illustrate the state of the art in herbal based compositions for promoting scalp and hair health and growth.

Edwards U.S. Pat. No. 604,111 discloses a hair tonic of mountain sage, glycerin, tincture of lobella, prickly pear juice, tincture of capsicum, sweet oil, and alcohol, which cleans the scalp, relaxes and stimulates the scalp, cools the scalp and gives the hair gloss.

McCarthur U.S. Pat. No. 3,932,611 discloses a composition for hair and scalp care comprising white petroleum jelly, beeswax, coconut oil, olive oil, castor oil, oil of sassafras and oil of cinnamon. The composition allegedly inhibits scaling of dandruff particles.

Pickford U.S. Pat. No. 4,002,734 discloses a composition for grooming or dressing hair comprising petroleum, rectified tar oil, phenol, sulfur, oxyquinoline, pine oil and castor oil in a petroleum jelly base. The composition allegedly inhibits scaling of dandruff particles.

Choy U.S. Pat. No. 4,230,689 discloses hydrating a mixture of rice with mung bean by heating at 75°-212° F. with a cup of Ginseng tea, recovering and condensing the vapors and using the condensate for grooming or dressing hair.

Faust U.S. Pat. No. 4,511,555 discloses a composition for grooming or dressing hair comprising an acceptable carrier, and a vegetable oil extract of sage, Indian hemp and rosemary. The composition is used in pomades and shampoos.

The present invention is distinguished over the prior art in general, and these patents in particular by providing a hair grooming composition which promotes scalp and hair health and growth comprises petroleum jelly, an oil extract of cactus, glycerin and oil of clover or other odorant. The petroleum jelly is heated in a pan with the cactus cut into small pieces and the mixture cooked until the cactus is brown and thoroughly extracted. The mixture is strained to remove cactus leaves and other solids and then mixed with glycerin and oil of clover. The product is then packaged for sale and use. The product improves scalp health and users have reported extensive regrowth of hair in bald areas.

SUMMARY OF THE INVENTION

It is therefore an object of the present invention to provide a new and improved hair grooming composition.

It is another object of this invention is to provide a new and improved hair grooming composition which improves scalp health.

Another object of this invention is to provide a new and improved hair grooming composition which improves scalp health and hair growth.

Another object of this invention is to provide a new and improved hair grooming composition which improves scalp health and promotes regrowth of hair in bald areas of the scalp.

Still another object of this invention is to provide a new and improved hair grooming composition containing extract of cactus which improves scalp health.

Still another object of this invention is to provide a new and improved hair grooming composition containing extract of cactus, petroleum jelly, glycerin and oil of clover which improves scalp health.

A further object of this invention is to provide a new and improved hair grooming composition containing extract of cactus, petroleum jelly, glycerin and oil of clover which improves scalp health and promotes regrowth of hair in bald areas of the scalp.

Other objects of the invention will become apparent from time to time throughout the specification and claims as hereinafter related.

The above noted objects and other objects of the invention are accomplished by a novel hair grooming composition which promotes scalp and hair health and growth comprises petroleum jelly, an oil extract of cactus, glycerin and oil of clover or other odorant. The petroleum jelly is heated in a pan with the cactus cut into small pieces and the mixture cooked until the cactus is brown and thoroughly extracted. The mixture is strained to remove cactus leaves and other solids and then mixed with glycerin and oil of clover. The product is then packaged for sale and use. The product improves scalp health and users have reported extensive regrowth of hair in bald areas.

DESCRIPTION OF A PREFERRED EMBODIMENT

A hair grooming composition which promotes scalp and hair health and growth is prepared by combining petroleum jelly, an oil extract of cactus (preferably Mexican cactus sold in grocery stores in Texas), glycerin and oil of clover or other odorant. The petroleum jelly is heated in a pan with the cactus cut into small pieces and the mixture cooked until the cactus is brown and thoroughly extracted. The mixture is strained to remove cactus leaves and other solids and then mixed with glycerin and oil of clover. The product is then packaged for sale and use.

A preferred example of preparation of this hair grooming composition is as follows:

One and one half pounds of Mexican cactus (obtained in grocery stores in Texas) was cut into small pieces for processing. Four pounds of pure (white) petroleum jelly were heated on an electric stove top range and the cactus pieces mixed in. The mixture was cooked until the cactus was brown. The solids, e.g., cactus leaves, undigested pieces of cactus, etc., were strained out. Then, 1.5 teaspoons glycerin and 1 teaspoon oil of clover were added and thoroughly stirred. The mixture was then cooled and packaged in jars for sale and use.

This product is an all-in-one hairdress. It can be used as a conditioner and also to promote hair growth in bald areas of the scalp. The product can be used prevent hair loss during chemical treatment of the hair. It has been used in conjunction with perm and straightening treatments and with dyeing. It has produced growth on the face and lips of men to promote growth of beards and mustaches. The product has also been used in promoting hair regrowth after having the head shaved for surgery. The product is applied to the treatment area once or twice a week for a period of one to four weeks with substantial hair growth resulting. It should not be used on the body or face unless hair is desired in those areas. If the hair has an excessive amount of split ends, the ends should be cut before commencing treatment.

This product has been field tested for many months by lay purchasers and by doctors. The product was applied by each user to the hair and particularly to bald areas of the scalp. Users report that the product improves scalp health and that extensive regrowth of hair has occurred in bald areas of the scalp. The utility of the product for this purpose has been attested to by a large number of users and pictures taken of each user before use and after a period of use.

While this invention has been shown fully and completely with special emphasis on certain preferred embodiments, it should be understood that within the scope of the appended claims the invention may be practiced otherwise than as specifically described herein.

I claim:

1. A hair grooming composition comprising
   a uniform cosmetic mixture of petroleum jelly, an oil extract of cactus, glycerin and an odorant, produced by cooking the cactus in admixture with said petroleum jelly to produce said oil soluble extract and then straining out solids and mixing in said glycerin and odorant.

2. A hair grooming composition according to claim 1 in which
   said odorant is oil of clover.

3. A hair grooming composition according to claim 1 in which
   said cactus is cooked in heated petroleum jelly until brown.

4. A hair grooming composition according to claim 1 in which
   said cactus is cut into small pieces and cooked in heated petroleum jelly until brown.

5. A hair grooming composition according to claim 4 in which
   said cactus is cooked in heated petroleum jelly at medium heat on an electric range until brown.

6. A hair grooming composition according to claim 1 in which
   said cactus is a Mexican cactus.

7. A hair grooming composition according to claim 1 in which
   the ingredients are combined and processed in the proportions of
   1.5 pounds of cactus cut into small pieces mixed into 4 pounds of heated petroleum jelly and cooked until the cactus is brown, straining out the solids, and adding in
   1.5 teaspoons glycerin and 1 teaspoon oil of clover, then stirring well and packaging.

8. A method of producing a hair grooming composition characterized by promoting scalp health and hair regrowth, which comprises
   cutting cactus cut small pieces,
   mixing said cactus pieces into heated into petroleum jelly and cooking until the cactus is brown and to produce and oil soluble cactus extract in said petroleum jelly,
   straining out the solids, and adding in glycerin and an odorant, then
   stirring well and packaging.

9. A method according to claim 8 in which
   the ingredients are combined and processed in the proportions of
   1.5 pounds of cactus cut into small pieces mixed into 4 pounds of heated petroleum jelly and cooked until the cactus is brown, straining out the solids, and adding in
   1.5 teaspoons glycerin and 1 teaspoon oil of clover, then
   stirring well and packaging.

10. A method according to claim 9 in which
    said cactus is cooked in heated petroleum jelly at medium heat on an electric range until brown.

11. A method according to claim 9 in which
    said cactus is a Mexican cactus.

12. A method of promoting hair and scalp health and hair growth in bald areas of the scalp which comprises applying to the hair and particularly the bald areas of the scalp a grooming composition comprising
    a uniform cosmetic mixture of petroleum jelly, an oil extract of cactus, glycerin and an odorant, produced by cooking the cactus in admixture with said petroleum jelly to produce said oil soluble extract and then straining out solids and mixing in said glycerin and odorant.

13. A method of promoting hair and scalp health according to claim 12 in which
    said odorant is oil of clover.

14. A method of promoting hair and scalp health according to claim 12 in which
    said cactus is cooked in heated petroleum jelly until brown.

15. A method of promoting hair and scalp health according to claim 12 in which
    said cactus is cut into small pieces and cooked in heated petroleum jelly until brown.

16. A method of promoting hair and scalp health according to claim 15 in which
    said cactus is cooked in heated petroleum jelly at medium heat on an electric range until brown.

17. A method of promoting hair and scalp health according to claim 12 in which
    said cactus is a Mexican cactus.

18. A method of promoting hair and scalp health according to claim 12 in which
    the ingredients are combined and processed in the proportions of
    1.5 pounds of cactus cut into small pieces mixed into 4 pounds of heated petroleum jelly and cooked until the cactus is brown to produce said oil soluble extract, straining out the solids, and adding in
    1.5 teaspoons glycerin and 1 teaspoon oil of clover, then
    stirring well and packaging.

* * * * *